(12) United States Patent
Wesselius et al.

(10) Patent No.: US 6,370,226 B1
(45) Date of Patent: Apr. 9, 2002

(54) CLINICAL X-RAY BASED APPARATUS AND METHOD WITH DYNAMIC SIGNALLING OF AN EXECUTION FEASIBILITY LEVEL DURING ENTERING OPERATIONAL PARAMETER VALUES

(75) Inventors: Jacob Hendrikus Wesselius; Aloysius Joannes Maria Bart; Johan Gerard Henri Rutgers; Maurice Hubertus Bernard Boumans, all of Eindhoven (NL)

(73) Assignee: U.S. Philips Corporation, New York, NY (US)

( * ) Notice: Subject to any disclaimer, the term of this patent is extended or adjusted under 35 U.S.C. 154(b) by 0 days.

(21) Appl. No.: 09/666,227

(22) Filed: Sep. 21, 2000

(30) Foreign Application Priority Data

Sep. 21, 1999 (EP) .............................. 99203084

(51) Int. Cl.⁷ ................................. H05G 1/54
(52) U.S. Cl. ......................... 378/118; 378/16
(58) Field of Search ............................ 378/16, 95, 97, 378/108, 117, 118, 207

(56) References Cited

U.S. PATENT DOCUMENTS

| 5,400,378 A | 3/1995 | Toth | ........................ 378/16 |
| 5,602,890 A | * 2/1997 | Gray et al. | .................... 378/57 |
| 5,917,929 A | * 6/1999 | Marshall et al. | ............ 382/128 |
| 6,081,750 A | * 6/2000 | Hoffberg et al. | .............. 700/17 |
| 6,280,084 B1 | * 8/2001 | Toth | ........................... 378/207 |

* cited by examiner

Primary Examiner—Robert H. Kim
Assistant Examiner—Jurie Yun

(57) ABSTRACT

A clinical XRAY based apparatus with a user interface is operated by initiating the apparatus and then entering a sequence of operational parameter values for as based thereon executing an XRAY irradiation process. In particular, during the entering an execution feasibility level of the process is dynamically ascertained in view of an anticipated physical or other quantitative effect on one or more critical elements of the apparatus. Upon detecting insufficient feasibility, one or more parameter values already entered are figured out that have a preponderantly negative effect on said feasibility level and a user-initiated amendment of their value or values is allowed, until raising the feasibility level to sufficient. Otherwise the entering is continued until completing the sequence as preliminary to executing the XRAY irradiation process.

10 Claims, 3 Drawing Sheets

CLINICAL X-RAY BASED APPARATUS AND METHOD WITH DYNAMIC SIGNALLING OF AN EXECUTION FEASIBILITY LEVEL DURING ENTERING OPERATIONAL PARAMETER VALUES

A clinical XRAY based apparatus and method with dynamical signalling of an execution feasibility level during entering operational parameter values.

BACKGROUND OF THE INVENTION

The invention relates to a system as recited in the preamble of claim 1. XRAY-based apparatuses are in wide use for diagnostic treatment, and in particular, but not limited to Computer Tomography Scanning. Before executing the measurements proper, an operator may have to select a variety of scan parameter values before the actual scan can be acquired. Inter alia because of the actual state of the apparatus, not all combinations of parameter values may be valid. The determining of whether a selected multi-parameter setting is feasible, represents a difficult task for a human operator, because of the following reasons:

Certain parameters are interdependent, such as through limitations imposed on certain geometrical movements. Also, the duration and the intensity of the radiation combine to produce the actual radiation load.

A particular aspect that is difficult to estimate is the dissipation load on critical elements such as the XRAY tube. The maximum incurred temperature is especially difficult to guess.

SUMMARY TO THE INVENTION

In consequence, amongst other things, it is an object of the present invention to allow the operator to dynamically anticipate the feasibility of a proposed radiation process, and in case the feasibility is too low, to amend the process in an early stage of the preparation thereof. In fact, if the feasibility level would be to low, the proposed irradiation could necessitate unforeseen wait times in order to let cool down the XRAY tube or other critical elements or other relaxation to occur. Various effects from outside could cause the XRAY tube to heat up, which herein is also called relaxation. Finally, in certain situations, the scan could even have to be aborted.

Now therefore, according to one of its aspects the invention is characterized according to the characterizing part of claim 1.

By itself, U.S. Pat. No. 5,400,378 has a feedback mechanism to the apparatus for under influence of varying tissue attenuations adjusting the XRAY dose. In this way, irradiated persons may be subjected to less radiation than otherwise. In practice, the user interface of the prior art apparatus would not signal this adjusting on the level of the irradiation parameter values for possible amending by an operator.

In contradistinction, the present invention is a procedure that affects the user interface in a dynamic manner, and in consequence, uses a calculated feasibility level of the process. In particular, the present invention allows to detect such problems in an early stage, so that mitigating steps could be taken, or alternatively, the process can be cancelled or directed to another, more powerful apparatus. In general, the present invention intends to greatly diminish delays that would be due to the trial and error setting of various parameter values in order to further improve the efficiency of the planning of scans.

The invention also relates to a clinical XRAY based apparatus arranged for applying the method as recited. Further advantageous aspects of the invention are recited in dependent claims.

BRIEF DESCRIPTION OF THE DRAWING

These and further aspects and advantages of the invention will be discussed more in detail hereinafter with reference to the disclosure of preferred embodiments, and in particular with reference to the appended Figures that show.

DETAILED DESCRIPTION OF PREFERRED EMBODIMENTS

Figure 1:
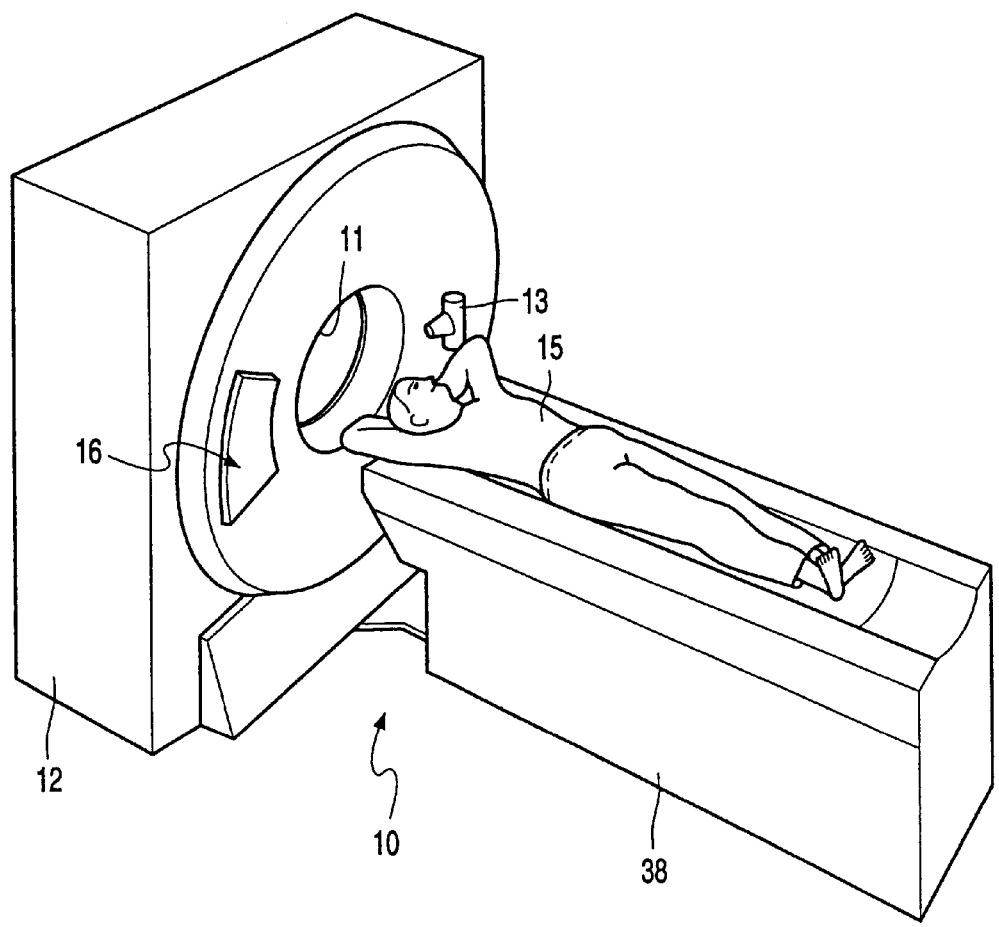
FIG. 1 is a pictorial view of a CT imaging system employing the present invention.

FIG. 1 is a pictorial view of a CT imaging system 10 for therein employing the present invention. Therein, gantry 12 has an XRAY source 13 that projects XRAY beam 14 towards detector array 16 on the opposite side of the gantry. Array 16 has a number of detector elements 18 that collectively sense the projected XRAYs that pass through clinical patient 15 who is resting on table 38. Each detector element produces an electric signal that represents its received XRAY intensity and, given the original XRAY intensity, an attenuation factor. During a scan to produce XRAY projection data, the gantry and associated components rotate about a center of rotation 19 that is located within patient 15. A reference detector not specifically shown at one end of array 16 measures the unattenuated beam intensity to detect non-uniformities in the applied XRAY dose.

Figure 2:
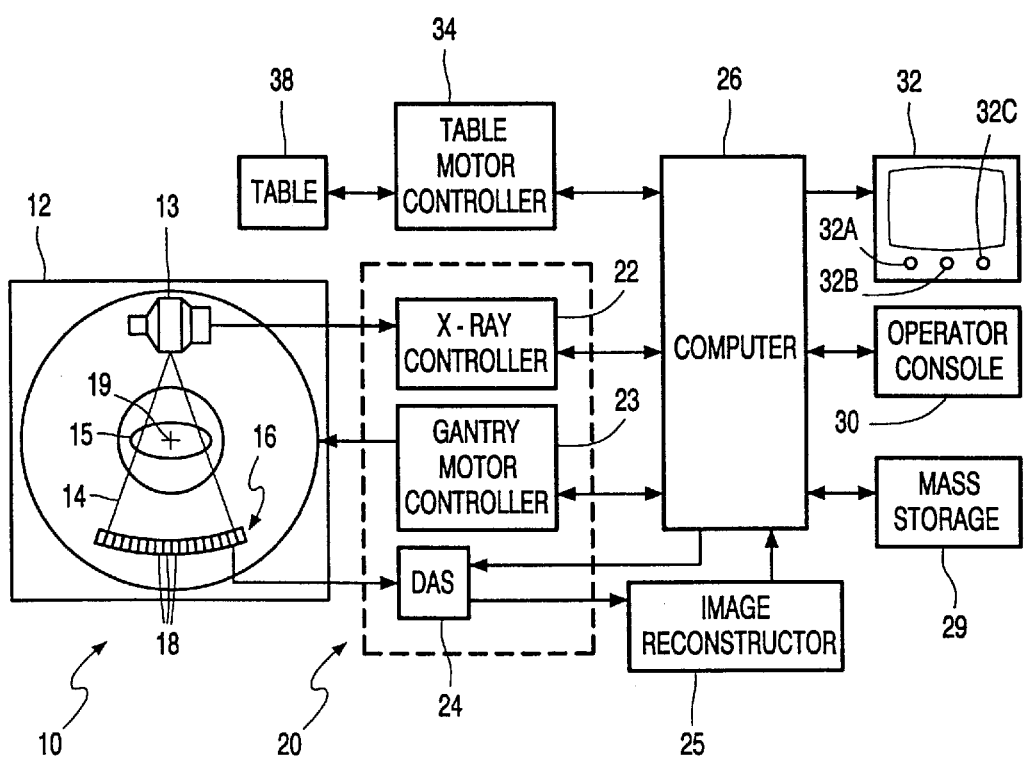
FIG. 2 is a block diagram of such system.

FIG. 2 is a block diagram of such a CT imaging system. Therein, the rotation of the gantry and the operation of source 13 are governed by control system 20. This mechanism comprises an XRAY controller 22 that provides power and timing signals to controller 23 that controls rotational speed and position of gantry 12. A data acquisition system 24 in the control mechanism samples analog data from detector elements 18 and executes A/D conversion. Image reconstructor 25 receives the digital XRAY data and executes image reconstruction. The reconstructed image is inputted into computer 26 for storage on mass storage device 29.

Computer 26 also receives commands and scanning parameters from an operator via user interface console 30 that may be provided with various input mechanisms, such as keyboard or mouse. User interface display 32 allows the operator to observe the reconstructed image and other data received from computer 26. The operator-supplied commands and parameters are used by computer 26 to provide control signals and information to the data acquisition system 24, to the XRAY controller 22, and to the gantry motor controller 23. Furthermore, computer 26 operates table motor controller 34 which controls motorized table 38 to position patient 15 in gantry 12.

In particular, computer 26 directs the various system components to carry out the prescribed scan in accordance with stored programs in dependency on a sequence of parameter values, such as angular or linear spacing between successive irradiation beams, irradiation time, XRAY energy, and various others that are well-known to persons skilled in the art.

In current systems, the validity of parameter values selected by the operator is only checked when all values have been entered and when the operator selects the next function that prepares the system for indeed executing the planned scan. At that instant, the system may signal an error message for warning that either the scan cannot be performed at all, or a warning message signalling that certain wait times will have to be introduced. Now, after receiving such error or warning message, the operator may want to change the parameters and repeat the procedure for inputting the various parameter values. Such is experienced by an operator as especially cumbersome, inter alia because a patient may actually be waiting on a table associated to the apparatus and further, because the patient will often have to be instructed about the process itself, such as on certain attitudes to assume, etcetera. However, this instruction should only been given when the planned scan has indeed been affirmed for execution.

The improvement through the present invention in the scan functionality is to provide on-line feedback on the validity of the selected parameter values. This means that:

a. After each change to a parameter value or to the system state, such as represented by heating up or cooling down of the XRAY tube, the validity is evaluated again and the feedback to the operator is updated.

b. In the embodiment, the validity may be indicated by a traffic light. Herein, green means that the scan may be executed. Next, yellow means that the scan may be executed after a certain wait time. Finally, red means that the scan cannot be executed at all. Instead of colors, other elementary signallings may be used such as icons or smiling/unsmiling faces. The graphical display of the planned acquisition on a scanogram image indicates by a color coding which slices and/or rotations cannot be acquired, or only after a waiting time.

The parameters checked in this functionality will cover various physical and other quantitative limitations of the system, such as the heat capacity of the XRAY tube, the available storage space on disc, the high voltage generator capacity, and the table positioning range. The functionality is based inter alia on a simulation of the heat dissipation of the XRAY tube during the acquisition of one scan series or a plurality thereof. The advantage of the present invention is that it will significantly shorten the feedback loop. In particular, an operator may select all parameter values in less time. Furthermore, the operator will get more insight in the cause of an insufficient feasibility level, which will allow to make better anticipations in later scan plannings.

Figure 3:
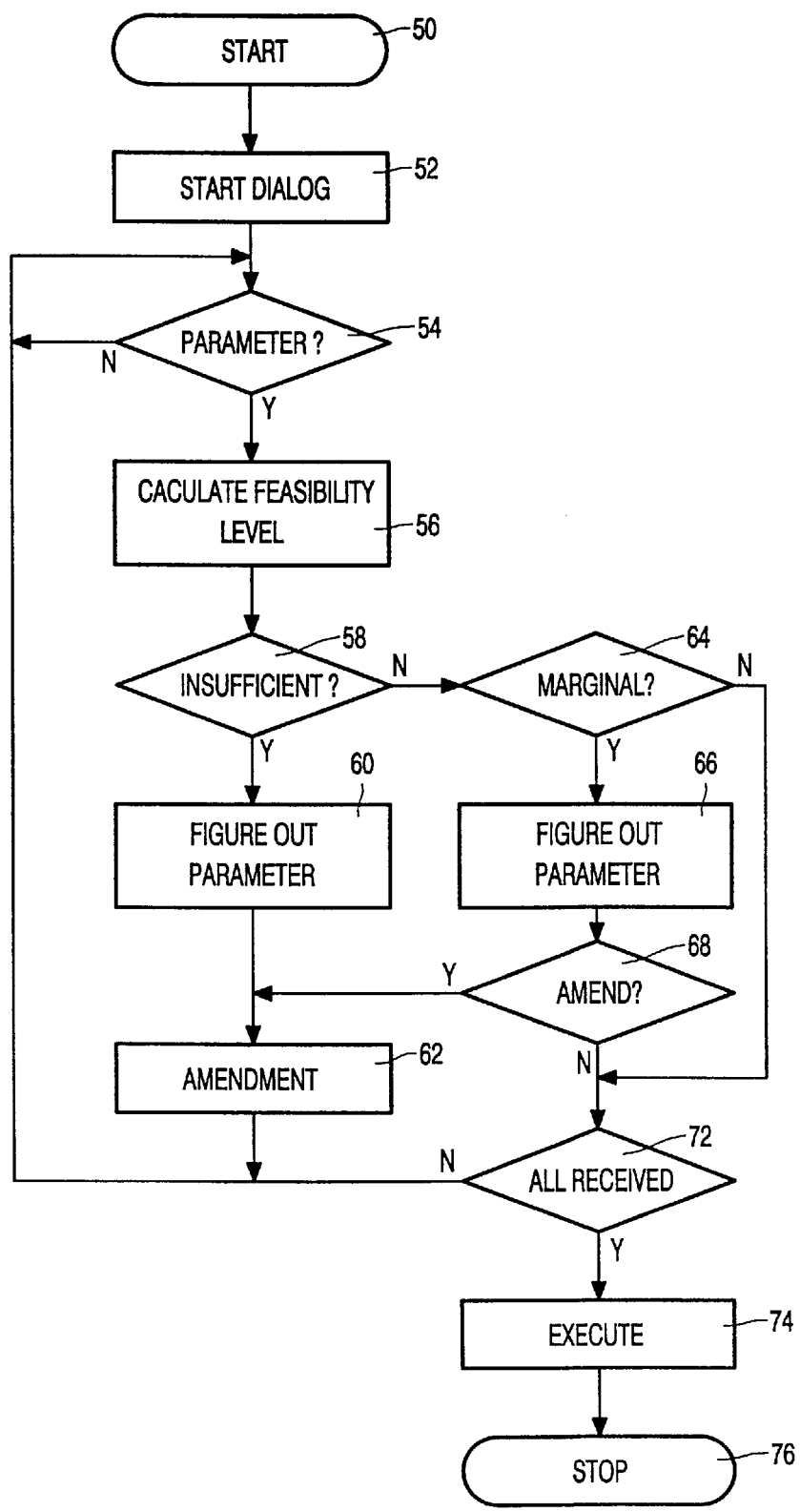
FIG. 3 is a flow chart explaining the present invention in more detail.

FIG. 3 is a flow chart explaining the present invention in more detail. In block 50, the procedure is started, and the required hardware and software facilities are assigned and initiated. In block 52, the user interface starts a dialog, such as through an appropriate welcome screen to the user. For enhanced clarity, the invention is being described through a form filling procedure, that presents a user with particular questions with respect to the specifying of parameters in a prescribed sequence. Highly skilled workers may employ a non-uniform sequence instead. In block 54, the system asks for a particular parameter value. If none is received (N), a waiting loop through block 54 is run continually. Upon receiving a parameter value (Y), the system in block 56 calculates an actual feasibility level as based on all parameter values that have already been received for the XRAY run to be executed next. If the feasibility level is insufficient (block 58, Y), this is signalled by a red color on indicator 32A in FIG. 32; such could also be done by a red sign or appropriate icon on screen 32. Now, the run cannot be executed, and the system in block 60 figures out one or more of the parameters that have a preponderantly negative effect on this feasibility level. If the thermal load on the tube would be too high, this could be the number of irradiation directions, the length of each radiation interval, or both parameter values combined. If the geometrical constraints would be violated, a single movement or a combination of two or more movements could be the culprit. In block 62 a complete or partial amendment is proposed, and the system returns to block 54. The amendment may identify the parameter value(s) that should be changed, and also by what amount.

If in block 58 the feasibility level was not fully insufficient (N), the level is checked in block 64 for marginal sufficiency. If true (Y), the run can only be executed with certain restrictions, such as one or more waiting intervals. In particular, the length of the waiting interval(s) could be indicated on the screen. In consequence, the system in block 66 figures out one or more of the parameters that have a preponderantly negative effect on the feasibility level. The system may display proposed parameter value amendment(s), and also, the effect thereof on the feasibility level, and/or effects on the waiting interval(s). In block 68, the user may choose whether to introduce an amendment or not. If positive (Y), in block 62 again a complete or partial amendment is proposed, with or without effects thereof on feasibility level, waiting interval(s), etcetera, and the system returns to block 54. Note that the operator may follow the proposal(s) for amendment in whole or in part, but may also try to improve by amendments outside the proposals. If the user does completely reject the possibility for amendment (N), for example, because the waiting time is deemed acceptable, the system goes to block 72.

If in block 64 the feasibility level is not marginal, but sufficient instead (N), this is signalled by a green color on indicator 32C, and the system goes to block 72. In block 72 the system detects whether the sequence of operational parameter values so far received is complete indeed. If negative (N), the system returns to block 54. If the sequence is complete (Y), the XRAY process is ready for execution (74), and subsequently, the operation is complete (block 76).

For clarity, in the embodiments various simplifications have been introduced, such as the omitting in FIG. 3 of measures to cope with operator errors, exit mechanisms, and various possible refinements. Generally, persons skilled will recognize amendments that are covered by the scope of the claims hereinafter.

What is claimed is:

1. A method for operating a clinical XRAY-based apparatus provided with user interface means, by initiating said apparatus and entering a sequence of operational parameter values for as based thereon executing an XRAY irradiation process;

said method being characterized by comprising the following steps:

during said entering dynamically ascertaining an execution feasibility level of said process in view of an anticipated physical or other quantitative effect on one or more critical elements of said apparatus;

upon detecting an insufficient feasibility level figuring out one or more parameter values already entered that have a preponderantly negative effect on said feasibility level, and allowing a user-initiated amendment of their parameter value or values, until raising said feasibility level to sufficient;

and otherwise continuing said entering until completing said sequence of operational value parameters as preliminary to executing said XRAY irradiation process.

2. A method as claimed in claim 1 for applying on a Computer Tomography System.

3. A method as claimed in claim 1, wherein an insufficient feasibility level is shown by a first user indication, a partially sufficient feasibility level is shown by a second user indication, and a fully sufficient feasibility level is shown by a third user indication.

4. A method as claimed in claim 1, wherein said feasibility level is updated through the entering and/or changing of a said parameter value, and also by an occurring physical relaxation process of said apparatus.

5. A clinical XRAY based apparatus arranged for applying a method as claimed in claim 1, said apparatus comprising user interface means, that are arranged for initiating said apparatus and entering a sequence of operational parameter values for as based thereon executing an XRAY irradiation process;

said apparatus being characterized by comprising ascertaining means for during said entering dynamically ascertaining an execution feasibility level of said process in view of an anticipated physical or other quantitative effect on one or more critical elements of said apparatus, amending means for upon detecting an insufficient feasibility level figuring out one or more parameter values already entered that have a preponderantly negative effect on said feasibility level, and allowing a user-initiated amendment of their parameter value or values, until raising said feasibility level to sufficient, and continue means for otherwise allowing to continue said entering until completion of said sequence of operational value parameters as preliminary to executing said XRAY irradiation process.

6. An apparatus as claimed in claim 5, being a Computer Tomography System.

7. An apparatus as claimed in claim 5, and having indicator means for showing an insufficient feasibility level by a first user indication, a partially sufficient feasibility level by a second user indication, and a fully sufficient feasibility level by a third user indication.

8. An apparatus as claimed in claim 7, wherein said indicator means show said indications through colors or icons.

9. An apparatus method as claimed in claim 5, and having updating means for updating said feasibility level through entering and/or changing of a said parameter value, and also by an occurring physical relaxation process of said apparatus.

10. An apparatus as claimed in claim 7, wherein said indicator means for a graphical display of a planned acquisition on a scanogram image are arranged for by a color coding indicating selective partial irradiations, such as slices and/or rotations which cannot be acquired, or only after a waiting time.

* * * * *